(12) United States Patent
Noack et al.

(10) Patent No.: US 7,368,464 B2
(45) Date of Patent: May 6, 2008

(54) PREPARATION FOR THE PRODUCTION OF 1,2,4-TRIAZOLYLMETHYL-OXIRANES

(75) Inventors: Rainer Noack, Großthiemig (DE); Michael Sander, Limburgerhof (DE); Michael Henningsen, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 548 days.

(21) Appl. No.: 10/516,727

(22) PCT Filed: Jun. 6, 2003

(86) PCT No.: PCT/EP03/05950

§ 371 (c)(1),
(2), (4) Date: Dec. 6, 2004

(87) PCT Pub. No.: WO04/000835

PCT Pub. Date: Dec. 31, 2003

(65) Prior Publication Data

US 2005/0176967 A1    Aug. 11, 2005

(30) Foreign Application Priority Data

Jun. 24, 2002    (DE) ................ 102 28 196

(51) Int. Cl.
*A61K 31/41*    (2006.01)
*C07D 249/08*    (2006.01)
(52) U.S. Cl. .................... 514/383; 548/262.2
(58) Field of Classification Search ............. 548/262.2; 514/383
See application file for complete search history.

(56) References Cited

U.S. PATENT DOCUMENTS

| 4,464,381 A | | 8/1984 | Janssen et al. | |
| 4,652,580 A | * | 3/1987 | Janssen et al. | ............. 514/383 |
| 4,906,652 A | * | 3/1990 | Karbach et al. | ............. 514/383 |
| 5,057,531 A | | 10/1991 | Seele et al. | |
| 5,102,899 A | | 4/1992 | Seele et al. | |
| 5,132,318 A | | 7/1992 | Seele et al. | |
| 5,268,517 A | | 12/1993 | Kober et al. | |

FOREIGN PATENT DOCUMENTS

| CA | 2 051 281 A | 3/1993 |
| CA | 1329995 A | 6/1994 |
| DE | 32 18 130 A1 | 11/1983 |
| DE | 35 36 529 A1 | 4/1987 |
| DE | 37 37 888 A1 | 5/1989 |
| DE | 38 05 376 A1 | 8/1989 |

(Continued)

OTHER PUBLICATIONS

Nachbaur et al., "1,2,4-triazole", Institut f. Anorg. Chemie der Universitat Graz, pp. 479-493.

(Continued)

*Primary Examiner*—Rebecca Anderson
*Assistant Examiner*—Susannah Chung
(74) *Attorney, Agent, or Firm*—Birch, Stewart, Kolasch & Birch, LLP

(57) ABSTRACT

The present invention relates to a process for the preparation of 1,2,4-triazol-1-ylmethyloxiranes of the formula I

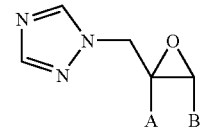

in which A and B are identical or different and, independently of one another, are $C_1$-$C_4$-alkyl, phenyl-$C_1$-$C_2$-alkyl, $C_3$-$C_6$-cycloalkyl, $C_3$-$C_6$-cycloalkenyl, tetrahydropyranyl, tetrahydrofuranyl, dioxanyl or phenyl, where the phenyl radical can carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, which comprises reacting
a) an oxirane of the formula II

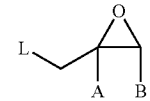

in which A and B have the meanings given above and L is a nucleophilically substitutable leaving group, with 4-amino-1,2,4-triazole of the formula III

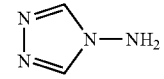

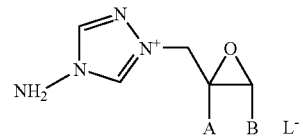

to give 4-amino-1,2,4-triazolium salts of the formula IV and
b) deaminating the 4-amino-1,2,4-triazolium salts IV with alkali metal nitrites and acid or organic nitrites to give 1,2,4-triazol-1-ylmethyloxiranes of the formula I, and to 4-aminotriazolium salts of the formula IV as intermediates.

19 Claims, No Drawings

FOREIGN PATENT DOCUMENTS

| | | | |
|---|---|---|---|
| DE | 38 06 089 A1 | 9/1989 |
| DE | 39 36 823 A1 | 5/1991 |
| EP | 0 094 564 A2 | 11/1983 |
| EP | 0 330 132 A1 | 8/1989 |
| EP | 0 334 035 A1 | 9/1989 |
| EP | 0 618 198 A | 10/1994 |
| WO | WO-94 02476 A | 2/1994 |

OTHER PUBLICATIONS

Astleford et al., "Synthesis of 1-alkyl-1,2,4-triazoles: A new one-pot regiospecific procedure", Journal of Organic Chemistry, 1994, vol. 54, pp. 731-732.

* cited by examiner

PREPARATION FOR THE PRODUCTION OF 1,2,4-TRIAZOLYLMETHYL-OXIRANES

The present invention relates to a process for the regiospecific preparation of 1,2,4-triazol-1-yl-methyloxiranes of the formula I

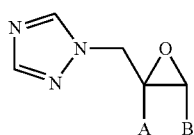

in which A and B are identical or different and, independently of one another, are $C_1$-$C_4$-alkyl, phenyl-$C_1$-$C_2$-alkyl, $C_3$-$C_6$-cycloalkyl, $C_3$-$C_6$-cycloalkenyl, tetrahydropyranyl, tetrahydrofuranyl, dioxanyl or phenyl, where the phenyl radical can carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, where
a) an oxirane of the formula II

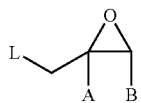

in which A and B have the meanings given above and L is a nucleophilically substitutable leaving group, is reacted with 4-amino-1,2,4-triazole of the formula III

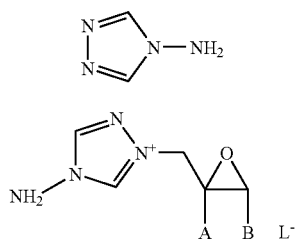

to give 4-amino-1,2,4-triazolium salts of the formula IV and
b) the 4-amino-1,2,4-triazolium salts IV are deaminated with alkali metal nitrites and acid or organic nitrites to give 1,2,4-triazol-1-ylmethyloxiranes of the formula I.

4-Aminotriazolium salts IV are intermediates for the preparation of azolylmethyloxiranes. Azolylmethyloxiranes are used for the manufacture of fungicidal compositions, in particular for combating cereal diseases.

EP-A 94 564, U.S. Pat. No. 4,906,652, EP-A 330132 and EP-A 334 035 disclose processes for the preparation of triazolylmethyloxiranes starting from an oxirane of the formula II and 1,2,4-triazoline presence of a base. All of the processes were carried out at room temperature. The reaction time is 8-18 hours.

DE-A 39 36 823 describes the reaction of oxirane II with sodium 1,2,4-triazolide in 5 h at 75° C. The solvents used are dimethylformamide and N-methylpyrrolidone.

The triazolation products present are worked up by precipitation with water and/or extraction.

The prior art processes are burdened with a series of disadvantages.

During the triazolation of compounds of the formula II, in addition to the desired 1-substituted triazoles, 4-substituted triazoles are also formed in amounts of 10-35%.

In addition, solvolysis and ring-opening reactions produce a number of by-products which reduce the yield and considerably impair isolation and purification of the desired triazolylmethyloxiranes.

To purify the isomer mixtures which forms, mention is made of:
extraction (e.g. DE-A 3218130, DE-A 3536529, DE-A 3805376, DE-A 3737888, EP-A 330132, U.S. Pat. No. 4,906,652), precipitation (e.g. DE-A 3936823), chromatography (e.g. DE-A 3806089, recrystallization from diisopropyl ether (DE-A 3936823, U.S. Pat. No. 4,906,652), methyl tert-butyl ether/n-hexane (DE-A 3805376, EP-A 330132), methyl tert-butyl ether (DE-A 3737888). In all cases various methods have to be combined.

The purity of the biologically effective isomers is predominantly less than 92%, only after complicated work-up as described above is it possible to achieve acceptable contents of more than 94%.

It is also known from the literature that during the alkylation of 4-aminotriazoles, quaternary triazolium salts IV are formed whose acyclic amino group can be deaminated analogously to the chemistry of correspondingly 1,1-substituted hydrazine derivatives, for example with sodium nitrite and HCl. Regioselectively substituted triazole derivatives are formed (Houben-Weyl, E 14,479ff).

This reaction can also be transferred to the alkylation with halomethyl ketones (Astleford et al. J. Org. Chem. 54,731 (1989) and is described for the preparation of antimycotic active ingredients, e.g. Can. Pat 2.051.281).

According to EP 618,198, oxiranes react with opening of the oxirane ring to give 2-hydroxyalkyl-4-aminotriazolium salts which can be deaminated, but then lead to 2-hydroxyalkyltriazoles.

According to the presented prior art, it could therefore not be expected that compounds of the formula II can be reacted with 4-aminotriazoles to give 4-aminotriazolium salts in which the oxirane ring is retained.

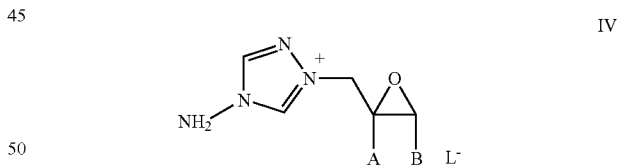

Surprisingly, one such process for the preparation of 1-substituted triazolylmethyloxiranes was found by using sterically hindered oxiranes II and reacting them with 4-aminotriazoles without or in the presence of catalysts or auxiliaries to give a quaternary ammonium salt IV, and then subjecting the nonalkylated 4-amino group to a deamination with alkali metal nitrites and an acid or organic nitrites. In this process, the desired 1-substituted triazolylmethyloxiranes forms without fractions of impurities or 4-substituted triazolylmethyloxiranes. The troublefree formation of the products according to the invention had not been expected since, firstly, a reaction of the aminotriazole with the oxirane ring to give hydroxyalkyltriazoles was expected and, secondly, the opening of the oxirane ring in the presence of a strong acid was also feared.

The process according to the invention is explained in more detail below.

For the process according to the invention, azolylmethyloxiranes which have been prepared from the following starting materials are suitable.

a) Oxiranes of the formula II in which A and B are identical or different and, independently of one another, are $C_1$-$C_4$-alkyl, phenyl-$C_1$-$C_2$-alkyl, $C_3$-$C_6$-Cycloalkyl, $C_3$-$C_6$-Cycloalkenyl, tetrahydropyranyl, tetrahydrofuranyl, dioxanyl or phenyl, where the phenyl radical may carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, and L is a nucleophilically substitutable leaving group. The oxiranes can be prepared as described in EP-A 94564, U.S. Pat. No. 4,906,652, EP-A 330132, EP-A 334035 and DE 3936823.

Preferred starting materials carry the following substituents, the preferences each applying on their own or in combination:

A and B are preferably a phenyl radical substituted by halogen, $C_1$-$C_4$-alkyl or $C_1$-$C_4$-alkyloxy.

Particularly preferably, A is 4-fluorophenyl and B is 2-chlorophenyl.

L is a nucleophilically substituted leaving group, such as, for example, halide, alkylsulfonate, arylsulfonate or alkyl sulfate. Preferably, L is chloride, bromide, tosylate and mesylate. L is particularly preferably mesylate.

b) 4-Amino-1,2,4-triazoles of the formula III or analogous derivatives.

The 4-aminotriazole used according to the invention is readily accessible from hydrazine and formamide (Houben-Weyl E 14,525).

The 4-aminotriazolium salts IV according to the invention are usually prepared in the presence of an organic solvent and optionally with the addition of a catalyst or an auxiliary at temperatures between 0-150° C., preferably 50-150° C.

Preferred organic solvents include alcohols, such as methanol, ethanol, butanols, isopropanol, pentanols, hexanols, octanols, decanols, methyl glycol, ethyl glycol, n-butyl glycol, ketones, such as acetone, methyl ethyl ketone or cyclohexanone, nitriles, such as acetonitrile or propionitrile, esters, such as ethyl acetate, butyl acetate, organic carbonates such as dimethyl carbonate or diethyl carbonate, non-aromatic and aromatic hydrocarbons such as cyclohexane, toluene, chlorobenzene or 1,2-dichlorobenzene, ethers, such as tetrahydrofuran, dimethoxyethane, dioxane, amides, such as dimethylformamide, dimethylacetamide, N-methylpyrrolidone, tetramethylurea, and also dimethyl sulfoxide, sulfolane and corresponding mixtures.

Suitable preferred organic solvents are alcohols, such as methanol, ethanol, isomeric butanols and pentanols, isopropanol, 2-ethylhexanol, methyl glycol, ethyl glycol, n-butyl glycol and mixtures thereof with toluene.

n-Butyl glycol, 2-ethylhexanol and mixtures thereof with toluene are particularly preferred.

Suitable catalysts are quaternary ammonium and phosphonium salts, such as tetrabutylammonium chloride, betaines, such as 4-dimethylsulfonium phenoxide. Suitable auxiliaries are specific nucleophilic anions, e.g. cyanide, iodide, fluoride, amines, such as DABCO, dimethylaminopyridine, dimethylcyclohexylamine, tributylamine, triethylamine or DBU.

The catalysts are used in amounts of 0.01-5 mol % based on the oxirane II, the auxiliaries in amounts of 5-300 mol %.

The 4-aminotriazolium salts of the formula IV can be obtained in pure form from the reaction mixtures by crystallization and/or precipitation, optionally at low temperatures below 10° C.

The 4-aminotriazolium salts of the formula IV are dissolved in water and treated with alkali metal nitrites, such as potassium nitrite or sodium nitrite and strong acids, such as hydrochloric acid or sulfuric acid, at −10-60° C. It is also possible to use organic nitrites, such as, for example, n-butyl nitrite or t-butyl nitrite.

Besides the aqueous solution, the deamination can also be carried out in aqueous/organic solvent mixtures, such as water/THF, water/alcohols or water/NMP.

In addition, it is possible to remove the solvents used by evaporation and to subject the residue to a deamination, where necessary following removal of the non-water-soluble components A particular-variant involves carrying out the aminotriazolation in a solvent which has low miscibility with water, such as n-butanol, isopentanol, 2-ethylhexanol or tetrabutylurea, with simultaneous or subsequent extraction of the quaternary salt with water.

The triazolylmethyloxiranes formed usually precipitate out of the aqueous solution during the deamination. The precipitation can be completed by neutralization.

As a result of the process according to the invention, the ratio of 1-substituted triazoles to 4-substituted triazoles (regioselectivity) is increased to a value of more than 50. 4-Substituted triazole derivatives can often no longer be detected.

The resulting product no longer needs to be purified in a complex manner. The content of 1-substituted triazole is usually greater than 98%.

The fraction of inactive isomers and by-products has been considerably reduced and thus the ecological efficiency of the agrochemical active ingredient is considerably increased.

The present invention further provides 4-amino-1,2,4-triazolium salts of the formula IV,

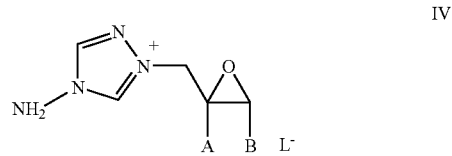

in which A and B are identical or different and, independently of one another, are $C_1$-$C_4$-alkyl, phenyl-$C_1$-$C_2$-alkyl, $C_3$-$C_6$-cycloalkyl, $C_3$-$C_6$-cycloalkenyl, tetrahydropyranyl, tetrahydrofuranyl, dioxanyl or phenyl, where the phenyl radical can carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, and in which L⁻ is the anion of a nucleophilically substitutable leaving group, such as, for example, halide, alkylsulfonate, arylsulfonate or alkyl sulfate.

A and B are preferably a phenyl radical substituted by halogen, $C_1$-$C_4$-alkyl or $C_1$-$C_4$-alkyloxy.

Particularly preferably, A is 4-fluorophenyl and B is 2-chlorophenyl.

Preferably, L⁻ is chloride, bromide tosylate and mesylate. L⁻ is particularly preferably mesylate.

The organic molecular moieties given for the substituents A, B and L represent collective terms for individual listings of the individual group members. All of the hydrocarbon chains, i.e. all alkyl, alkoxy, haloalkyl, phenylalkyl, cycloalkyl, cycloalkenyl chains, may be straight-chain or branched.

Unless stated otherwise, halogenated substituents preferably carry one to five identical or different halogen atoms. The meaning halogen is in each case fluorine, chlorine, bromine or iodine.

In addition, the following meanings, for example, apply:

$C_1$-$C_4$-alkyl: e.g. methyl, ethyl, propyl, 1-methylethyl, butyl, 1-methylpropyl, 2-methylpropyl or 1,1-dimethylethyl;

$C_1$-$C_2$-haloalkyl: a $C_1$-$C_2$-alkyl radical, as mentioned above, which is substituted partially or completely by fluorine, chlorine, bromine and/or iodine, thus e.g. chloromethyl, dichloromethyl, trichloromethyl, fluoromethyl, difluoromethyl, trifluoromethyl, chloromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl.

$C_1$-$C_4$-alkoxy: e.g. methoxy, ethoxy, propoxy, 1-methylethoxy, butoxy, 1-methylpropoxy, 2-methylpropoxy or 1,1-dimethylethoxy;

phenyl-$C_1$-$C_2$-alkyl: $C_1$-$C_2$-alkyl substituted by a phenyl radical, such as benzyl, 1-phenylethyl and 2-phenylethyl;

$C_3$-$C_6$-cycloalkyl: e.g. cyclopropyl, cyclobutyl, cyclopentyl or cyclohexyl;

$C_3$-$C_6$-cycloalkenyl: such as $C_3$-$C_6$-cycloalkyl with a double bond, such as cyclopropenyl, cyclobutenyl, cyclopentenyl or cyclohexenyl.

The process according to the invention is described by the examples below.

As oxirane II, in all cases a compound of the formula II with the following substituents is used: L=$CH_3SO_2O$—, B=4-fluorophenyl and A=2-chlorophenyl.

EXAMPLE 1

142.8 g of compound II (L=MeSO$_2$O—, cis/trans 5:95) are heated to 100° C. with 33.6 g of 4-amino-1,2,4-triazole and 400 ml of n-butanol for 8 h. The aminotriazolium salt formed precipitates out of the reaction mixture in solid form. The conversion with regard to mesylate is more than 90% (HPLC method). After the mixture has been cooled, 110 g of 4-aminotriazolium salt IV can be separated off (62% yield). The mother liquor can be used with the aminotriazolium salt which remains in solution (ca. 45 g) for a further batch.

The 4-aminotriazolium salt has an m.p.=192° C.

EXAMPLE 2

142.8 g of compound II (L=MeSO$_2$O—, cis/trans 5:95) are dissolved in 500 ml of isopropanol and then heated for 8 h at 80° C. with 33.6 g of 4-aminotriazole. A conversion of compound II of 51% is achieved, and about 72 g of 4-aminotriazolium salt IV (80% of the reacted compound II) can be separated off from the cooled solution. The m.p. is 193° C.

An analogous experiment in the presence of 0.2 g of potassium iodide reaches a conversion of 67% after 8 h.

EXAMPLE 3

454 ml of mesylate-DMF solution, comprising 143 g of mesylate II (cis/trans 5:95) are heated at 130° C. with 33.6 g of 4-amino-1,2,4-triazole and 400 ml of N-methylpyrrolidone for 2 h. The aminotriazolium salt IV formed can, after the solvent has been removed with reduced pressure, be purified by careful washing of the residue with acetone/MeOH. The conversion with regard to mesylate is greater than 97% (HPLC method). 140 g of 4-aminotriazolium salt IV can be isolated (81% yield). The 4-aminotriazolium salt IV has an m.p.=190° C.

EXAMPLE 4

A mixture of 5 g (14 mmol) of mesylate and 1.4 g (17 mmol) of 4-amino-1,2,4-triazole in 20 g (153 mmol) of 2-ethylhexanol is stirred for 16 h at 80° C. 50 g of the mineralized water are then added and, after 5 min at 65° C., the phases are separated. Yield (quant. HPLC): 85%.

EXAMPLE 5

A mixture of 5 g (14 mmol) of mesylate and 1.1 g (13 mmol) of 4-amino-1,2,4-triazole in 20 g (148 mmol) of diglyme is stirred for 7 h at 80° C. 50 g of demineralized water are then added and, after 5 min at 65° C., the phases are separated. Yield (quant. HPLC): 25%.

EXAMPLE 6

A mixture of 5 g (14 mmol) of mesylate and 1.4 g (17 mmol) of 4-amino-1,2,4-triazole in 20 g (202 mmol) of N-methylpyrrolidone is stirred for 7 h at 100° C. 50 g of demineralized water are then added and, after 5 min at 65° C., the phases are separated. Yield (quant. HPLC): 72%.

EXAMPLE 7

A mixture of 5 g (14 mmol) of mesylate and 1.4 g (17 mmol) of 4-amino-1,2,4-triazole in 20 g (149 mmol) of diethylene glycol dimethyl ether is stirred for 7 h at 100° C. 50 g of demineralized water are then added and, after 5 min at 65° C., the phases are separated. Yield (quant. HPLC): 51%.

EXAMPLE 8

A mixture of 5 g (14 mmol) of mesylate and 1.4 g (17 mmol) of 4-amino-1,2,4-triazole in 20 g (203 mmol) of cyclohexanone is stirred for 6 h at 90° C. 50 g of demineralized water are then added and, after 5 min at 65° C., the phases are separated. Yield (quant. HPLC): 2%.

EXAMPLE 9

A mixture of 5 g (14 mmol) of mesylate and 1.4 g (17 mmol) of 4-amino-1,2,4-triazole in 20 g (153 mmol) of 1-octnol is stirred for 6 h at 80° C. 50 g of demineralized water are then added and, after 5 min at 65° C., the phases are separated. Yield (quant. HPLC): 65%.

EXAMPLE 10

A mixture of 5 g (14 mmol) of mesylate and 1.4 g (17 mmol) of 4-amino-1,2,4-triazole in 20 g (227 mmol) of ethylene carbonate is stirred for 6 h at 80° C. 50 g of demineralized water are then added and, after 5 min at 65° C., the phases are separated. Yield (quant. HPLC): 27%

EXAMPLE 11

A mixture of 5 g (14 mmol) of mesylate and 1.4 g (17 mmol) of 4 amino-1,2,4-triazole in 20 g (194 mmol) of benzonitrile is stirred for 6 h at 80° C. 50 g of demineralized water are then added and, after 5 min at 65° C., the phases are separated. Yield (quant. HPLC): 49%

EXAMPLE 12

A mixture of 5 g (14 mmol) of mesylate and 1.4 g (17 mmol) of 4-amino-1,2,4-triazole in 20 g (200 mmol) of cyclohexanol is stirred for 17 h at 80° C. 50 g of demineralized water are then added and, after 5 min at 65° C., the phases are separated. Yield (quant. HPLC): 29%

EXAMPLE 13

A mixture of 5 g (14 mmol) of mesylate and 1.4 g (17 mmol) of 4-amino-1,2,4-triazole in 20 g (136 mmol) of 1,2-dichlorobenzene is stirred for 16 h at 80° C. 50 g of demineralized water are then added and, after 5 min at 65° C., the phases are separated. Yield (quant. HPLC): 21%

EXAMPLE 14

At 90° C. and 130 mbar, 356.8 g (1.0 mol) of mesylate in 2020 g of toluene are metered into a solution of 252.2 g (3.0 mol) of 4 amino-1,2,4-triazole in 1070.4 g (8.4 mol) of n-butyl glycol. Metering and distillation are complete after a minimum of 6 h and then left to cool to 85° C. The temperature is then decreased to 65° C. with a ramp of 3 K/h. After cooling the resulting mash to 25° C., the suspension is then filtered through a suction filter Yield (quant. HPLC): 98%

EXAMPLE 15

At 90° C. and 130 mbar, 121 g (0.34 mol) of mesylate in 679 g of toluene are metered into a solution of 86.4 g (1.03 mol) of 4-amino-1,2,4-triazole and 128.3 g of tri-n-butylamine (0.69 mol) in 600 g g (4.7 mol) of n-butyl glycol. Metering and distillation of 556 g are complete after a minimum of 6 h and then left to cool to 85° C. The temperature is then decreased to 65° C. with a ramp of 3 K/h. After cooling the resulting mash to 25° C., the suspension is then filtered through a suction filter. Yield (quant. HPLC): 77%

EXAMPLE 16

At 90° C. and 130 mbar, 121 g (0.34 mol) of mesylate in 679 g of toluene are metered into a solution of 86.4 g (1.03 mol) of 4-amino-1,2,4-triazole and 43.2 g of tri-n-butylamine (0.34 mol) in 600 g g (4.7 mol) of n-butyl glycol. Metering and distillation of 556 g are complete after a minimum of 6 h and then left to cool to 85° C. The temperature is then decreased to 65° C. with a ramp of 3 K/h. After cooling the resulting mash to 25° C., the suspension is then filtered through a suction filter. Yield (quant. HPLC): 52%

EXAMPLE 17

At 90° C. and 130 mbar, 128.2 g (0.36 mol) of mesylate in 725 g of toluene are metered into a solution of 84.8 g (1.01 mol) of 4-amino-1,2,4-triazole in 600 g (4.7 mol) of n-butyl glycol. Metering and distillation of 631 g of toluene are complete after a minimum of 6 h and then left to cool to 85° C. The temperature is then decreased to 65° C. with a ramp of 3 K/h. After cooling the resulting mash to 25° C., the suspension is then filtered through a suction filter. Yield (quant. HPLC): 99%

Deamination:

EXAMPLE 18

Procedure 50 mmol of solid 4-aminotriazolium salt IV (22 g,. A=4-fluorophenyl and B=2-chlorophenyl) are taken up in 150 ml of water and admixed with 110 mmol of conc. hydrochloric acid (11 ml). The mixture is then cooled to 0° C. A solution of 3.6 g (52 mmol) of sodium-nitrite in 50 ml of water is slowly added dropwise at this temperature during which a gentle evolution of gas starts. When the addition is complete, the mixture is left to warm to room temperature and then neutralized with dilute potassium carbonate solution (~50 ml of a 15% strength aqueous solution). The product which precipitates out is filtered off with suction, washed with water and dried.

Yield: 95%, m.p. 136° C., content: 98.5% trans-epoxyconazole (trans based on A and B).

EXAMPLE 19

Under nitrogen, 1162.5 g (0.5 mol) of 18.9% strength aqueous triazolium salt solution are initially introduced and the pH is adjusted to <1.0 using 18% strength hydrochloric acid. The reaction mixture is heated to 60° C. Then, in parallel, 250 ml (0.8 mol) of 20% strength sodium nitrite solution (1.6 eq) and 80 g (0.39 mol) of 18% strength hydrochloric acid (0.8 eq) are metered in at pH 1 over a period of 1 h. The suspension is then stirred for 1.5 h at 60° C., cooled to 20° C. and neutralized with 15% strength NaOH. The suspension is then separated off via a suction filter and the solid is dried in the vacuum drying cabinet at 20 mbar and an internal temperature of 50° C. Yield (quant. HPLC): 87.8%

EXAMPLE 20

Under nitrogen, 214 g (0.05 mol) of 10.8% strength aqueous triazolium salt solution are initially introduced. The reaction mixture is heated to 50° C. 7.0 g (0.065 mol) of n-butyl nitrite are then metered in over a period of 1 h. The suspension is then stirred for 1 h at 50° C., cooled to 20° C. and separated off via a suction filter and the solid is dried in the vacuum drying cabinet at 20 mbar and an internal temperature of 50° C. Yield (quant. HPLC): 49.0%

EXAMPLE 21

Under nitrogen, 940 g (0.13 mol) of 6.1% strength aqueous triazolium salt solution are initially introduced and the pH is adjusted to <1.0 using 18% strength hydrochloric acid. The reaction mixture is heated to 60° C. Then, in parallel, 61.3 ml (0.2 mol) of 20% strength sodium nitrite solution (1.5 eq) and 29 g (0.39 mol) of 18% strength hydrochloric acid (1.1 eq) are then metered in at pH 1 over a period of 1 h. The suspension is then stirred for 1.5 h at 60° C., cooled to 20° C. and separated off via a suction filter and the solid is dried in the vacuum drying cabinet at 20 bar and an internal temperature of 50° C. Yield (quant. HPLC): 92.7%

EXAMPLE 22

Extraction 142.8 g of compound II are dissolved in 500 ml of n-butanol and then heated for 7 h with 33.6 g of 4-aminotriazole. A conversion of compound II of 83% is achieved. Following the addition of 100 ml of toluene, the organic phase is extracted with 3×500 ml of water. The aqueous solution is cooled to 0-5° C., acidified with 160 ml of 18% HCl and then admixed in portions with a solution of 27.6 g of sodium nitrite in 100 ml of water ($N_2O$ evolution). During this admixing, a white precipitate forms which, after washing with MeOH/water and drying at 80° C., gives 65 g of isomer-free trans-poxyconazole. From the mother liquor it is possible, following neutralization with 2N NaOH, to obtain about a further 18 g of impure epoxyconazole.

Yield of pure product based on compound II: 59.3%, content: 97.9% trans-epoxyconazole, m.p. of 136° C.

The organic phase can be used for a further batch, the toluene added being recovered by distillation and only added again during the extraction.

EXAMPLE 23

142.8 g of compound II are dissolved in 500 ml of n-butanol and then heated for 12 h with 33.6 g of 4-aminotriazole. A conversion of compound II of 97% is reached. Following the careful removal of the solvent at 8 mbar and 60° C., the residue is dissolved in 1000 of water and unreacted compound II is extracted twice with 100 ml of toluene.

The aqueous solution is cooled to 0-5° C., acidified with 160 ml of 18% HCl and then admixed in portions with a solution of 27.6 g of sodium nitrite in 100 ml of water ($N_2O$ evolution). During the admixing, a white precipitate forms. After 4 h, the mixture is neutralized with potassium carbonate solution and filtered with suction. After washing with MeOH/water and drying at 80° C., 143 g of isomer-free trans-epoxyconazole are obtained.

Yield: 83% m.p. 136° C. Content: 98.7%

EXAMPLE 24

Extractive One-pot Reaction

Procedure:

35.6 g of compound II (L=$MeSO_2O$—, cis/trans 5:95, 100 mmol) are taken up in 200 ml of tetrabutylurea and admixed with 8.8 g (105 mmol) of 4-amino-1,2,4-triazole and 200 ml of water with the addition of tetrabutylammonium chloride. The mixture is then refluxed for 4 hours (conversion based on compound II about 30%). During this time, the reaction product dissolves in the aqueous phase, while unreacted alkyl compound and excess aminotriazole remains in the immiscible organic phase. The mixture is cooled and the aqueous phase is separated off. The organic phase can be returned.

The aqueous phase is admixed with 2.2 times the molar amount of conc. hydrochloric acid and cooled to 0° C. The corresponding molar amount of sodium nitrite, dissolved in 50 ml of water, is slowly added dropwise at this temperature, during which gentle gas evolution starts. When the addition is complete, the mixture is warmed to room temperature and then neutralized with dilute potassium carbonate solution. The product which precipitates out is filtered off with suction, washed with water and dried.

Yield (based on alkyl compound used): 8.2 g of trans-epoxyconazole (80% based on reacted compound II).

We claim:

1. A process for the preparation of 1,2,4-triazol-1-yl methyloxiranes of the formula I

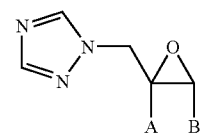

in which A and B are identical or different and, independently of one another, are $C_1$-$C_4$-alkyl, phenyl-$C_1$-$C_2$-alkyl, $C_3$-$C_6$-cycloalkyl, $C_3$-$C_6$-cycloalkenyl, tetrahydropyranyl, tetrahydrofliranyl, dioxanyl or phenyl, where the phenyl radical can carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, which comprises reacting a) an oxirane of the formula II

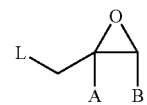

in which A and B have the meanings given above and L is a nucleophilically substitutable leaving group, with 4-amino-1,2,4-triazote of the formula III

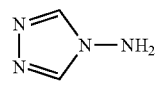

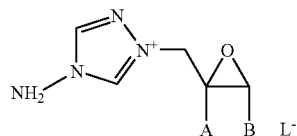

to give 4-amino-1,2,4-triazolium salts of the formula IV and b) deaminating the 4-amino-1,2,4-triazolium salts IV with alkali metal nitrites and acid or organic nitrites to give 1,2,4-triazol-1-yl methytoxiranes of the formula I.

2. A process as claimed in claim 1, wherein the reaction in stage a) is carried out in the presence of an organic solvent.

3. A process as claimed in claim 2, wherein alcohols, ketones, nitriles, esters, organic carbonates, nonaromatic and aromatic hydrocarbons, ethers, amides, dimethyl sulfoxide, sulfolane or mixtures thereof are used as organic solvent.

4. A process as claimed in either claim 1 or 2, wherein the organic solvent used is methanol, ethanol, butanols, isopropanol, pentanols, hexanols, octanols, decanols, methyl glycol, ethyl glycol, n-butyl glycol, acetone, methyl ethyl ketone, cyclohexanone, acetonitrile, propionitrile, ethyl acetate, butyl acetate, tetrahydrofuran, dimethoxyethane, dioxane, dimethylformamide, dimethylacetamide, N-methylpyrrolidone, tetramethylurea, dimethyl sulfoxide, sulfolane or mixtures thereof.

5. A process as claimed in claim 4, wherein the organic solvent used is n-butyl glycol, 2ethylhexanol or mixtures thereof with toluene.

6. A process as claimed in claim 1, wherein the reaction in stage a) is carried out at temperatures of from 50 to 150° C.

7. A process as claimed in claim 1, wherein the reaction in stage a) is carried out in the presence of 0.01-5 mol % of a catalyst or 5-300 mol % of an auxiliary.

8. A process as claimed in claim 7, wherein quaternary ammonium salts, quaternary phosphonium salts and betaines are used as catalyst and/or nucleophilic anions and amines are used as auxiliaries.

9. A process as claimed in any of claims 7 to 8, wherein tetrabutylammonium chloride and 4-dimethylsulfonium phenoxide are used as catalyst and/or cyanides, iodides, fluorides, 1,4-diaza-bicyclo[2.2.2]octan (DABCO), dimethylaminopyridine, dimethylcyclohexylamine, tributylarnine, triethylamine or 1,8-diaza-bicyclo[5.4.0]-7-undecen (DBU) are used as auxiliaries.

10. A process as claimed in claim 1, wherein the 4-aminotriazolium salts of the formula IV formed in stage a) are separated off from the reaction mixture by precipitation and/or crystallization.

11. A process as claimed in claim 10, wherein the precipitation and/or crystallization of the 4-aminotriazolium salts of the formula IV is carried out at temperatures below 10° C.

12. A process as claimed in claim 1, wherein the 4-aminotriazolium salts of the formula IV formed in stage a) are extracted from the reaction mixture by continuous and/or discontinuous extraction.

13. A process as claimed in claim 12, wherein the continuous and/or discontinuous extraction is carried out with water, optionally in the presence of a water-immiscible organic solvent.

14. A process as claimed in claim 1, wherein the deamination in stage b) is carried out in aqueous solution, water/tetrahydrofuran, water/alcohols or water/N-methyl-2-pyrrolidone.

15. A process as claimed in claim 1, wherein the deamination in stage b) is carried out with organic nitrites in aqueous or organic solution or in aqueous/organic solvent mixtures such as water/tetrahydrofuran, water/alcohols, water/N-methyl-2-pyrrolidone.

16. A process as claimed in either claim 14 or 15, wherein the deamination in stage b) is carried out at a temperature of from −10 to 60° C.

17. A 4-amino-1,2,4-triazolium salt of the formula IV

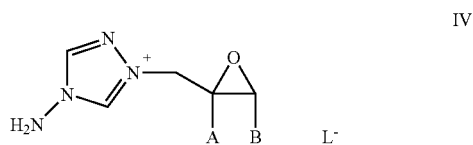

wherein A and B are identical or different and, independently of one another, are $C_1$-$C_4$-alkyl, phenyl-$C_1$-$C_2$-alkyl, $C_3$-$C_6$-cycloalkyl, $C_3$-$C_6$-cycloalkenyl, tetrahydropyranyl, tetrahydrofuranyl, dioxanyl or phenyl, where the phenyl radical can carry one to three substituents chosen from the group: halogen, nitro, $C_1$-$C_4$-alkyl, $C_1$-$C_4$-alkyloxy, phenoxy, amino, $C_1$-$C_2$-haloalkyl or phenylsulfonyl, and wherein L is a nucleophilically substitutable leaving group.

18. The 4-amino-1,2,4-triazolium salt of the formula IV as claimed in claim 17, in which A and B are identical or different and are a phenyl radical substituted by halogen, $C_1$-$C_4$-alkyl or $C_1$-$C_4$-alkoxy.

19. The 4-amino-1,2,4-triazolium salt of the formula IV as claimed in claim 17, in which A is 4-fluorophenyl and B is 2-chlorophenyl.

* * * * *